US00PP29219P3

(12) United States Plant Patent
Probasco et al.

(10) Patent No.: US PP29,219 P3
(45) Date of Patent: Apr. 10, 2018

(54) HOP PLANT NAMED 'HBC 472'

(50) Latin Name: *Humulus lupulus*
Varietal Denomination: HBC 472

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 14/756,965

(22) Filed: Nov. 2, 2015

(65) Prior Publication Data

US 2016/0360660 P1 Dec. 8, 2016

Related U.S. Application Data

(60) Provisional application No. 62/230,415, filed on Jun. 4, 2015.

(51) Int. Cl.
*A01H 5/00* (2006.01)

(52) U.S. Cl.
USPC ..... Plt./236

(58) Field of Classification Search
USPC ..... Plt./236
CPC ..... A01H 5/00
See application file for complete search history.

*Primary Examiner* — Kent L Bell
(74) *Attorney, Agent, or Firm* — Svendsen Legal, LLC

(57) ABSTRACT

A new hop plant named 'HBC 472' is disclosed. The cones of 'HBC 472' mature in September. 'HBC 472' is used for its aromatic quality.

4 Drawing Sheets

CROSS-REFERENCE TO RELATED APPLICATIONS

Priority is claimed with respect to U.S. Provisional Patent Application 62/230,415 filed on Jun. 4, 2015.
Genus and species: *Humulus lupulus*.
Variety denomination: 'HBC 472'.

STATEMENT REGARDING FEDERALLY SPONSORED RESEARCH OR DEVELOPMENT

None

BACKGROUND OF THE INVENTION

'HBC 472' is a product of a controlled breeding program carried out by the inventors in the Yakima Valley of Washington State. 'HBC 472' is a result from the pollination of 'YCR 123' (unpatented *Humulus lupulus*, var. *neomexicanus* female plant) with a mix of pollen from selected males. The cross pollination was made in 2004. The plant was selected and assigned accession number 472 in 2008. At this time, it was asexually reproduced via softwood cuttings in a greenhouse near Toppenish, Wash. Prior to 2014, the original single plant of 'HBC 472' was expanded to multiple plants, which were planted in the area of Toppenish, Wash. By 2014, the plants had been observed and evaluated for several years. Throughout several generations of asexual propagation, 'HBC 472' has been observed to retain its distinctive characteristics and remain true to type.

COMPARISON OF 'HBC 472' TO PARENT PLANT AND COMARISON CULTIVAR

'HBC 472's parent plant was a *H. lupulus*, var. *neomexicanus* female. Little is known about the plant beyond one year of data collected. The plant has since died. Table 1. sets forth some of the distinguishing characteristics of 'HBC 472' as compared to its female parent 'YCR 123', and to the 'Cascade' cultivar as a closely comparable cultivar.

TABLE 1

| | Instant Plant | Mother Plant | Cascade |
|---|---|---|---|
| ID#: | 'HBC 472' | 'YCR 123' | — |
| UV Alpha: | 7-9% | 2-4% | 5.5-9.0% |
| UV Beta: | 7-9% | 7-9% | 6.0-7.5% |
| Alpha:Beta: | 1:1 | 1:2.5 | 1.1 |
| % Co—H: | 45-50% | 50% | 30-35% |
| Matures: | 9/21-10/1 | >10/1 | 9/5-9/15 |

BRIEF DESCRIPTION OF THE PHOTOGRAPHS

Figure 1:
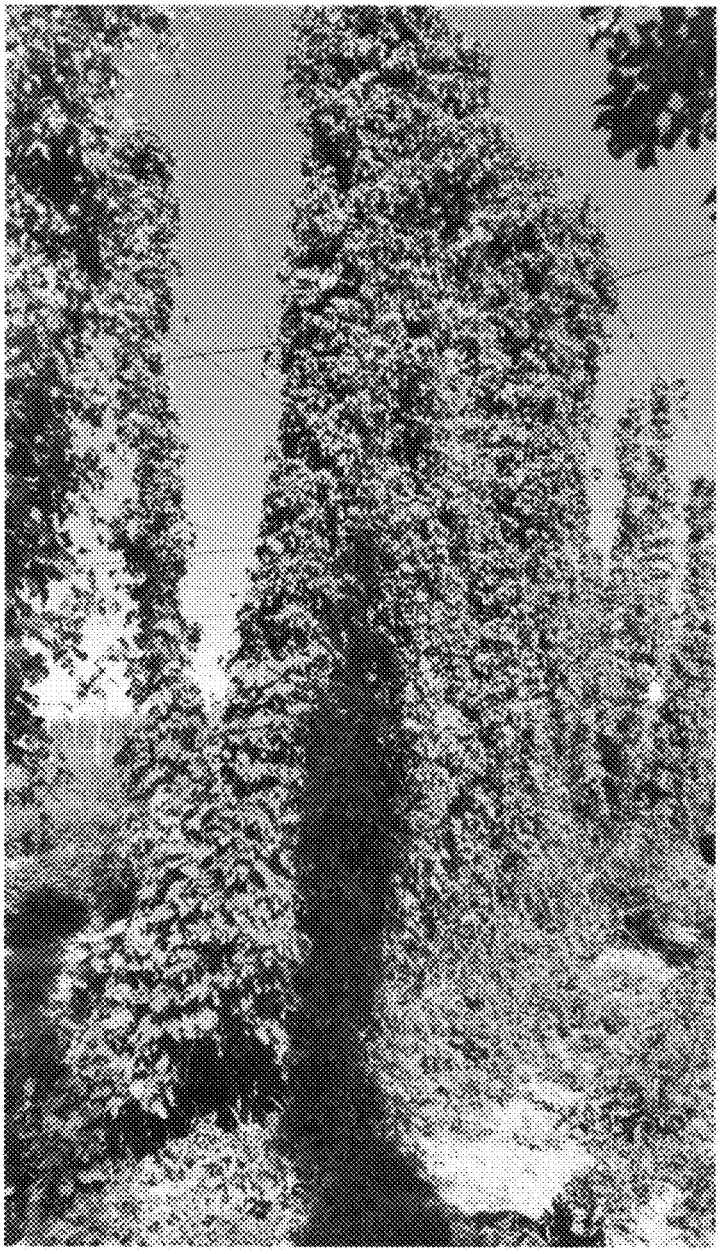
FIG. 1 illustrates a mature 'HBC 472' hop plant grown on a trellis.
Figure 2:
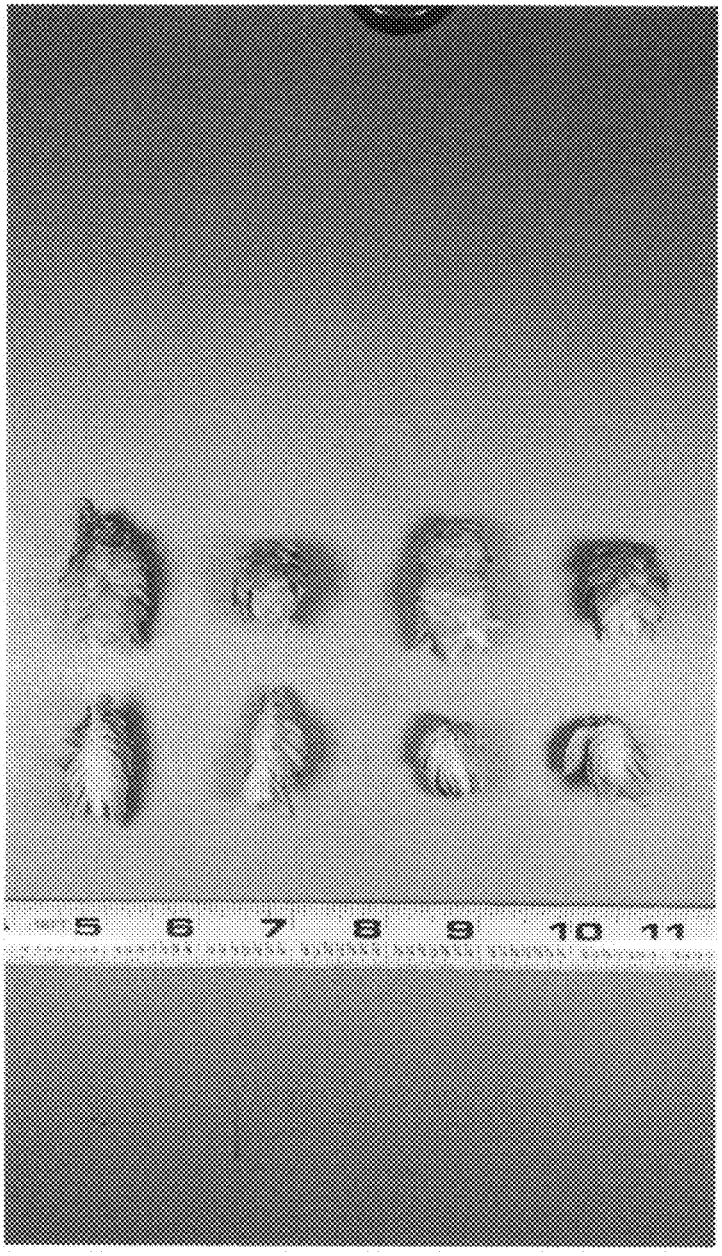
FIG. 2 illustrates whole cones and cross sections of cones of the 'HBC 472' hop plant.
Figure 3:
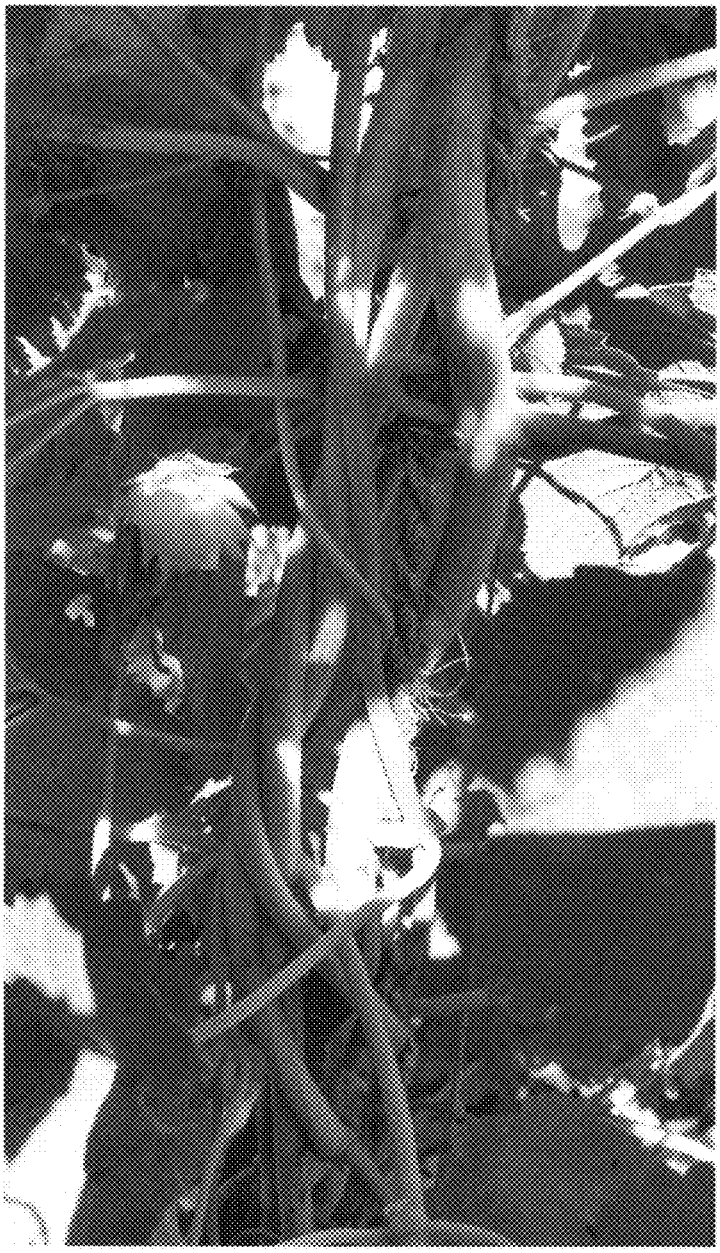
FIG. 3 illustrates the bine of a mature 'HBC 472' hop plant.
Figure 4:
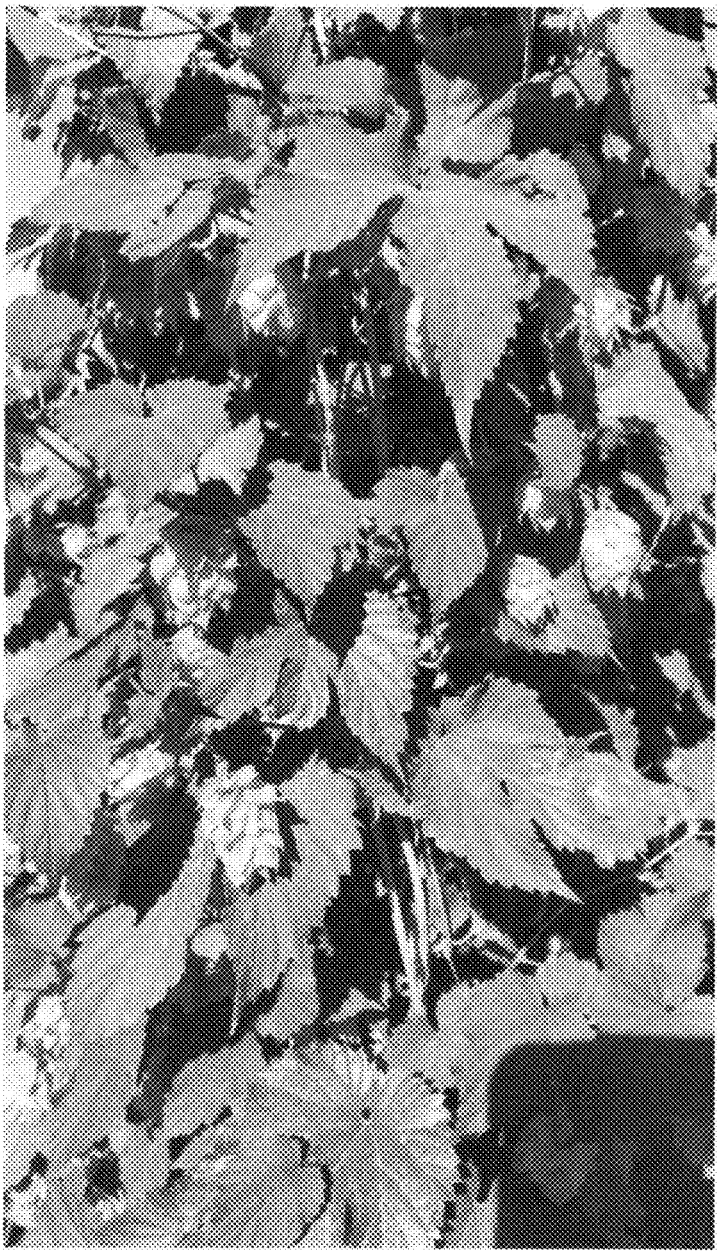
FIG. 4 illustrates the cones and leaves of a mature 'HBC 472' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2013-2014 growing seasons at Toppenish, Wash.

It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on The Royal Horticultural Society Colour Chart.

Use: Brewing.

Harvest date: September (during 2013 to 2014 growing seasons at Toppenish, Wash.).

Ploidy: Diploid, 2n=2x.

Disease susceptibility: Moderate resistance to powdery mildew. Susceptible to downy mildew.

Crop yield: 1300-1700 lb per acre. 1450-1800 kg per hectare.

Plant shape: Climbing bine, columnar growth.

Bine:

*Color*.—Yellow Green 146B.
*Stipule direction*.—Down and forked (as observed on May 8$^{th}$).
*Stipule color*.—Yellow green 143C.
*Avg. number stipules per bine*.—Two per Node.
*Stripe present*.—Present but faint.
*Stripe color*.—Red Purple 60A.
*Bine diameter*.—9.4 mm at base and 8.3 mm at nine feet.
*Bine length*.—Grown on an 18 ft trellis, typical growth 18-25 ft.
*Length between internodes*.—6.7 cm.
*Lateral length between internodes*.—200-210 mm on average.
*Lateral length*.—60 cm-150 cm.
*Lateral diameter*.—2-4 mm at the base and 0.5-1 mm at the terminus.
*Lateral color*.—144B.

Leaf:

*Arrangement*.—Opposite.
*Shape*.—Cordate and palmate.
*Apex*.—Acuminate.
*Average length of mature leaf*.—16.0-17.5 cm.
*Average width of mature leaf*.—13.50-16.50 cm.
*Base*.—Cordate.
*Venation pattern*.—Palmate.
*Serrations per inch*.—5-10.
*Color of mature leaf upper surface*.—Yellow Green 146A.
*Color of mature leaf lower surface*.—Yellow Green 147A.
*Color of immature leaf upper surface*.—Yellow Green 147A.
*Color of immature leaf lower surface*.—Green 137B.
*Number of lobes*.—1-7.
*Margin*.—Serrate.
*Petiole length*.—Average 9-10 cm.
*Petiole diameter*.—2-4 mm at the base.
*Color*.—146D.

Cone:

*Weight*.—500-950 mg.
*Shape*.—Ovate.
*Length*.—35 mm.
*Diameter*.—22 mm.
*Pickability*.—Good pickability.

Bract:

*Shape*.—Orbicular.
*Length*.—6-11 mm.
*Width*.—4-9 mm.
*Apex*.—Acuminate.
*Margin*.—Entire.
*Base*.—Rounded.
*Color upper*.—Yellow-green 144B.
*Color lower*.—Yellow-green 144B.

Bracteole:

*Shape*.—Ovate.
*Length*.—4-5 mm.
*Width*.—3-4 mm.
*Color upper*.—Yellow-green 154D.
*Color lower*.—Yellow-green 154D.

Lupulin glands:

*Shape*.—Pedunculated Oblong Polyps.
*Moderate number of lupulin glands per cone*.

Analytical characteristics:

*Alpha acid* (*as % of cone weight*).—7.5-9.6%.
*Beta acid* (*as % of cone weight*).—7.1-8.8%.
*Cohumulone* (*as % of alpha acids*).—47-49%.
*Total oil*.—1.5-2 mL per 100 g hops.
*Myrcene*.—33-41%.
*Humulene*.—0.64-1.4%.
*Caryophyllene*.—26-30%.
*Farnesene*.—3.8-6%.
*Linalool*.—0.18-0.2%.
*Storage stability*.—90% to 95% alpha acids remaining after 6 months storage at room temperature.

The invention claimed is:

1. A new and distinct Hop plant as illustrated and described herein.

* * * * *